United States Patent [19]
Gustafson

[11] Patent Number: 5,924,422
[45] Date of Patent: Jul. 20, 1999

[54] ORAL DEVICE TO AID WEIGHT CONTROL

[76] Inventor: Lynn Gustafson, 17 Tapiola Ct., Rockville, Md. 20850

[21] Appl. No.: 08/963,498

[22] Filed: Nov. 3, 1997

[51] Int. Cl.⁶ .......................................................... A61F 5/37
[52] U.S. Cl. ............................................ 128/846; 128/859
[58] Field of Search ...................... 128/846, 848, 128/859–862; 602/902; 433/7

[56] References Cited

U.S. PATENT DOCUMENTS

| | | | |
|---|---|---|---|
| 3,277,892 | 10/1966 | Tepper | 128/860 |
| 4,471,771 | 9/1984 | Steven | 128/859 |
| 4,738,259 | 4/1988 | Brown | 128/859 |
| 4,883,072 | 11/1989 | Bessler | 128/859 |

*Primary Examiner*—Michael A. Brown
*Attorney, Agent, or Firm*—Donald A. Kettlestrings

[57] ABSTRACT

An oral device and method for slowing down the rate of food ingestion, thereby aiding digestion, assimilation, and allowing time for raising blood sugar and achieving satiety sooner, with less food consumption over a given period of time. The device consists of any means for lowering the normally vaulted area of the roof of the mouth. In the preferred embodiment, the vault lowering means includes a molded piece which fits against the palate, and retaining wires to secure the piece to the teeth, while avoiding interference with the teeth on occlusion. The method and apparatus for lowering of the vault reduces the amount of food which can be comfortably ingested per bite. In use, the device allows the user to freely move his tongue and jaws, to talk, to breath, to drink, and to chew food. The method includes altering temporarily the configuration of the palate by lowering the vaulted area of the roof, to reduce the volume in the mouth available for food and reducing the food intake.

15 Claims, 1 Drawing Sheet

ORAL DEVICE TO AID WEIGHT CONTROL

BACKGROUND OF THE INVENTION

1. Field of the Invention

The present invention relates generally to artificial weight control devices, and more particularly to an oral device to aid in weight control. More specifically, the invention relates to an oral device which assists in weight control by reducing the volume of a user's oral cavity to slow down the rate of food ingestion.

2. Related Art

Methods and apparatuses for controlling weight are known. The methods include dieting, exercising, body wrapping, special medications, stomach and bowel surgery, blocking the intake of solid food by wiring shut the mouth, or by use of a sieve-like mouth guard. The most effective method of weight control, of course, is to merely limit the amounts of calories that are taken into one's digestive system. Thus, dieting, and the variations thereof, including fasting, are perhaps the most widespread and well-known methods of weight control.

Various mechanical devices and oral appliances also are known in the art to assist in weight control. These include elastic devices which are attached over the mouth to inhibit, but not completely prevent food intake, and still permit normal breathing and speech, as disclosed in U.S. Pat. Nos. 4,825,881 and 4,883,072, to Bessler. Another device design is merely positioned in the mouth to stimulate salivation and swallowing, such as disclosed in U.S. Pat. Nos. 3,224,442 and 5,052,410, both issued to Stubbs. Others are designed to be placed adjacent to or over the teeth, to impede chewing action and thus reduce food intake. U.S. Pat. Nos. 4,727,867 (Knoderer) and 4,738,259 (Brown et al.) describe examples of such devices. Steven et. al. (U.S. Pat. No. 4,471,771) disclose a sieve-like device which is pivotally supported on upper teeth and drop down every time the mouth is open, to block the intake of solid food. Only liquids and finely-ground food may pass.

Although use of an oral weight control device such as Steven et al. does, in fact, limit intake to liquids and semi-liquids only, it poses problems for the user. First, the device is cumbersome and must stay in the mouth constantly. There can be psychological complications as it requires the user to adapt to a large moving object inside the mouth at all times. This adaption may not be possible for all users, and could create tension, nervousness, and self-consciousness over long periods of time. Due to the permanent nature of its installation in the mouth, relief from these problems may not be available. Psychologically, the permanent device acts as a crutch since the user does not exercise free will in its daily use. The habit of its function also is out of step with the normal daily occurrence of ingesting solid food. Thus, it keeps the user from partaking in any average meal, and does not serve to train the user to change any pattern or habit that created the weight gain.

Secondly, physiological problems would include abrasion of the tongue from the repeated contacts with the device. The abrasion problem extends to the sides of the cheeks due to constant friction, especially during talking. Thirdly, oral hygiene can not be optimal because the device and attaching mechanism are not readily removable. Even though the teeth may be brushed in some fashion, complete and total hygiene can not be easily achieved. Food particles remaining in the mouth even after brushing will collect in the mouth and attach to the many crevices of the device. Since the device drops down on the tongue as the mouth is opened, flossing of the rear teeth is not possible, thus further contributing to poor oral hygiene and dental health. Bacteria accumulating in the mouth causes halitosis and illness.

Furthermore, medication and nutritional supplements in capsule or tablet form could not be ingested in the usual fashion. In the event of a medical emergency, this could pose additional problems which can not be readily overcome due to the permanent nature of the device's installation in the mouth.

Published research has shown that under normal conditions, there is a lag time between the entry of food into the digestive track and the assimilation of nutrition into the blood stream. For example, it takes approximately 20 minutes from the time that the food reaches the stomach for it to be broken down so that it can be absorbed into the blood stream. This, then, carries the message of nourishment to the hunger centers of the brain, triggering a response of being full. Therefore, the rapid ingestion of food until the hunger sensation is satisfied, will invariably lead to excessive caloric intake. Additional information regarding these phenomena can be found in *Optimal Wellness*, by Dr. Ralph Golan, Ballantine Books, 1995. In discussing food digestion and assimilation, Dr. Golan states that "Ideally, you should eat slowly and take small bites, making sure to chew thoroughly." In *Manifesto for a New Medicine*, Dr. James S. Gordon (Addison Wesley, 1996) states: "Most of us eat too fast, as well as too much. Almost 70 million Americans are more than 20% above their ideal weight." In *Eat More, Weigh Less*, Harper Perennial, 1993, Dr. Dean Ornish recommends smaller bites, eaten slowly, peacefully.

For these reasons, it is generally recommended that solid food be consumed slowly. Taking smaller bites make for slower eating, giving the digestion process time to register satiety, thus slowing the rate of consumption and the amount of food consumed.

Published research states that a habit can be established by consistently altering behavior patterns for 21 days. Thus, if a person can develop a habit of eating smaller bites and at a slower rate, with the aid of a removable device, for example, then eventually the user will be able to consume food in a healthier manner even when not using the device.

Other studies show that most people expect to eat for a given, set period of time, regardless of the amount of food that they ingest. This being true, then if a person can obtain the satisfaction of having a "full mouth" with less food present, then that person would consume less food per bite, slowing down the process, aiding digestion and reducing the amount of food needed for satisfaction.

SUMMARY OF THE INVENTION

The invention relates to an apparatus and method for improvement of digestion, assimilation, and regulation of food, and more particularly, for a mold-made device to fit the individual user so as to slow down the rate of food ingestion, and the amount of food ingested. It is therefore an object of the present invention to provide an oral device to aid weight control adapted to be installed by the user at the time of ingestion of food, which reduces the space in the oral cavity by a device which lowers the vault of the roof of the mouth.

Another object of the present invention is to provide such an oral device which allows the user to freely ingest normal food, while slowing down the quantity rate of consumption per swallow.

Another object of the present invention is to allow the user to develop a habit of eating smaller bites at a slower rate, so that eventually the user will be able to consume food in a healthier manner, even when not using the device.

A further object of the present invention is to provide the user with the satisfaction of having a full mouth, with less food present.

Yet another object of the invention is to provide such a diet aid device that allows the user to maintain optimal oral hygiene since the device is easily removed and easily cleaned. It does not impede any regular oral hygiene.

These and other objects of the invention are realized in an oral device made of a light weight material, molded to fit the user's upper palate, and which functions to alter the palate to a low-vault state. The device is secured by a wire extending from each side, with the free end of each wire extending between two adjacent teeth on each side of the upper mouth, while the natural suction between the material and the lining of the palate holds the device in place. The device needs only to be worn during the consumption and ingestion of food, although it may be left in the mouth continually, without affecting speech, swallowing, drinking, or other customary movements of the mouth. By lowering the palate vault, the device reduces the volume of the oral cavity and thus slows the ingestion of food. The device is not permanently attached in the mouth, and is readily removable, thus permitting the user to practice complete oral hygiene at all times. Moreover, the device does not impede the user from taking oral medications in the form of tablets or capsules.

The present invention is a novel type of oral weight control or diet aid. It offers a temporary altering of the anatomy of the mouth. In use, it is painless, effortless, hygienic and individualized. The device physically resembles a conventional orthodontic retainer. However, an orthodontic retainer functions primarily to apply forces to the teeth, and is not intended nor designed to build up the palate, nor to reduce the volume of the mouth in order to reduce food consumption. To the contrary, the design and intent of the orthodontic retainer is to minimize interference with the normal functions in the mouth. Orthodontic retainer-like devices have been proposed which are positioned against the palate for such purposes as correcting tongue thrusting problems or to inhibit thumb sucking. Again, these devices were not designed for weight control.

Other objects and features and additional advantages of the invention will be apparent from the foregoing and the following description and discussion, in conjunction with the accompanying drawings.

DETAILED DESCRIPTION OF THE INVENTION

Figure 1:
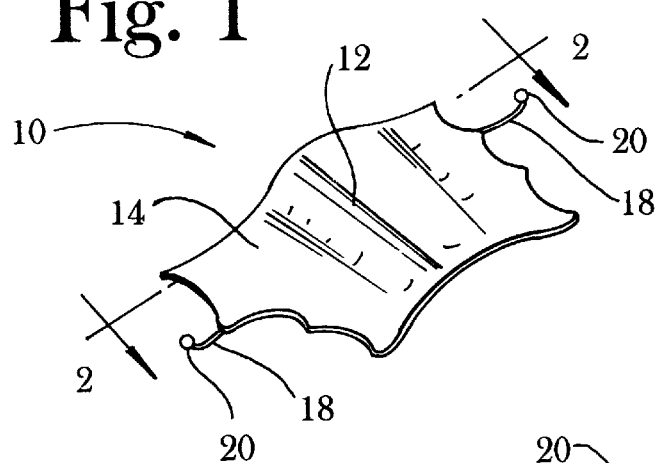
FIG. 1 is a perspective view of an oral weight control device according to the present invention.
Figure 2:
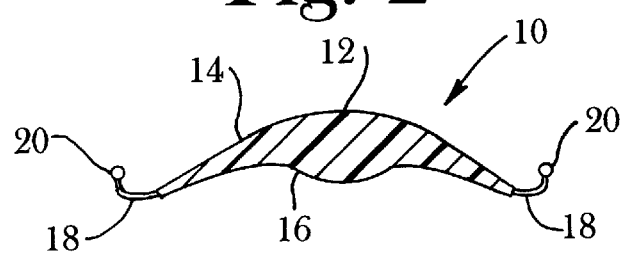
FIG. 2 is a cross section of the device along view line 2—2 in FIG. 1.

As shown in FIG. 1, an oral weight control device according to the present invention, identified generally by the reference character 10, resembles an orthodontic retainer, and has a central, thickened portion 12 which is molded to fit the contours and configuration of the user's mouth. The upper surface 14 of the device is configured to exactly fit the roof of the user's mouth, while the lower surface 16 is configured to replicate the roof, or palate, of the user's mouth. The center portion 12 creates a prosthesis or an imitation of a low-vaulted palate condition. Note FIG. 2. When worn, the device 10 effectively lowers the roof of the user's mouth, toward the tongue, to reduce the overall volume of the oral cavity. The amount by which the volume of the oral cavity is reduced is determined by the thickness of the device 10, and can be established in consultation with a health professional fitting the device to the user, such as a medical doctor, a dentist or an orthodontist. A device with a thinner central portion 12 would be appropriate for a person having a smaller mouth, or otherwise does not require as much reduction in oral cavity volume. A device with a thicker central portion 12 would be appropriate for a person with a larger mouth or requires a greater reduction in oral cavity volume.

Thicker central portion 12 in device 10 has a region of increased thickness located toward the back of the user's mouth and a region of reduced thickness located toward the front of the user's mouth when device 10 is positioned in the user's mouth as described herein. See FIG. 1.

A short wire 18 is embedded on each lateral side of the device 10, with the end terminated by an appropriately-sized ball 20 to form a "ball clasp". The wire 18 is slipped between two adjacent teeth in each side of the upper mouth, with the ball 20 bearing against the outer surfaces of the teeth to attach the device 10 and support it against the palate. Use of the wire permits the weight control device 10 to be quickly, easily and securely positioned against the roof of the user's mouth when desired, and to be quickly and easily removed after use or for cleaning. If necessary, one or more additional wires (not shown) may be embedded in the device, spaced along the length of the device 10, and similarly shaped as the wire 18, to provide additional attachment points for the device to ensure a secure fit in the mouth. In place of two, separate short lengths of wire on the sides of the device, a single longer length of wire (not shown) may be embedded within the thickness of the device, with the free ends extending from the sides thereof. Of course, other attachment means may be used which would permit ready attachment and removal of the device. Instead of the balls 20, for example, appropriately-sized circular-shaped rings or loops (not shown) which encircle the teeth in the upper mouth, one tooth on each side, can be used to provide semi-permanent attachment of the device.

Figure 4:
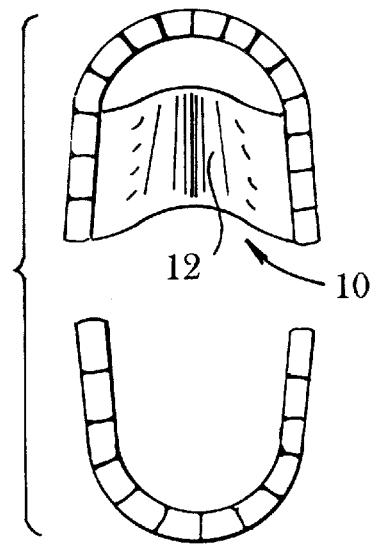
FIG. 4 is a partial schematic showing the roof of a mouth with the device of FIG. 1 in place.

The weight control device 10 can be made of any lightweight material which is appropriate for the interior of the mouth, such as materials commonly available and used in orthodontics, and is individually molded to provide a secure, comfortable fit for the user. The device 10 is appropriately dimensioned and contoured along the sides to fit comfortably against the teeth, and does not extend too far toward the back of the mouth where it may interfere with the air passages from the nasal cavity or with swallowing. Note FIG. 4. Techniques commonly used by orthodontists and dental lab technicians may be used to fabricate the device and to secure the attachment wire or wires.

Figure 3:
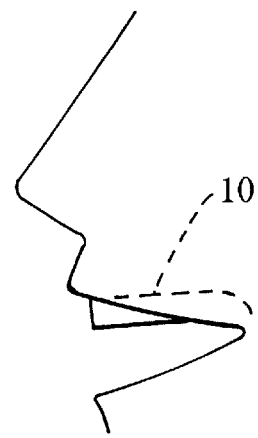
FIG. 3 is a partial schematic showing the orientation of the device of FIG. 1 when worn by a user.

The device 10 can be easily and quickly put into use, without any special training, by positioning it in the mouth, with the upper surface 14 against the palate, and pushing the wire 18 between the corresponding teeth, so that the balls rest on the outer surfaces of the teeth. When correctly positioned, as shown in FIG. 3, the device does not interfere with either the tongue or the teeth, in biting, chewing, swallowing or talking. The device 10 functions to lower the natural palate surface, and does not require any conscious effort by the user to achieve its purposes.

When the device is in place in the mouth, it creates a condition known as a "low-vaulted palate" wherein the roof of the mouth is not as highly vaulted as it might be otherwise. The user finds that smaller amounts of food are taken per bite to eat comfortably, and that less food need to be consumed to obtain the feeling of satisfaction that one gets from having a "full mouth". With the reduced volume in the mouth provided by the device, the user will require longer periods of time to eat a certain amount of food, and will tend to be satisfied with less food for an equivalent eating time. The reduced volume in the mouth leads to reduced food consumption, which leads to weight loss. Initially, the user may be tempted to eat at more frequent intervals, possibly out of habit. However, the on-going benefits of the device continue since the rate of food consumption will be reduced, and the longer time required to consume the food will cause the user to reach the point of hunger satisfaction sooner, thus reducing the total amount of food consumed. Over a relatively short period of time, the user's stomach will shrink, further reducing the desire for food and reaching the point of hunger satisfaction sooner.

With consistent use of the device, the user will easily and relatively quickly develop the habit of taking smaller bites when eating, and consuming smaller amounts of food. At some point, the habit will be sufficiently ingrained that the user can discontinue the use of the device. Alternatively, the use of the device can be continued to reinforce and/or maintain the beneficial habits.

The inventor has conducted evaluation tests of the device, and results have shown that a person using the device can adjust to wearing it in a short period of time, and that it does not affect or interfere with normal activities, such as talking, laughing, swallowing, drinking (although in reduced quantities with each swallow), brushing of the teeth and, since it is readily removable, observance of good oral hygiene. Persons using the device have been able to realize steady, consistent weight loss.

Among the other important features of the invention are that the device requires no special training for its use, and once it is in place there is no requirement imposed upon the user for its proper and effective operation.

Although not specifically described herein or illustrated in the drawings, numerous modifications and variations of the present invention are possible in light of the above disclosure. It is therefore to be understood that within the scope of the invention defined in the appended claims the invention may be practiced otherwise than as specifically described herein.

I claim:

1. A device for weight control by reducing the rate of food consumption, comprising:
   a molded element positionable against the roof of a user's mouth to temporarily alter the configuration of the palate whereby the food-containing volume of the mouth is reduced and the quantity of food per bite is reduced;
   said molded element defining a central, thickened portion for lowering the normally vaulted area of the roof of the mouth, said central, thickened portion being thicker than remaining portions of said molded element; and
   means attached to said molded element for removably supporting said molded element in fixed relationship against the roof of the mouth.

2. A device according to claim 1, wherein said molded element is molded to conform to the contours of the roof of the mouth.

3. A device according to claim 2, wherein said molded element has a portion of reduced thickness located toward the front of the mouth and a portion of increased thickness located toward the back of the mouth when said molded element is removably positioned in fixed relationship against the roof of the mouth.

4. A device according to claim 1, wherein said supporting means includes a second element for connection to the teeth adjacent to the roof of the mouth.

5. A method for weight control by reducing the rate of food consumption, comprising fixedly positioning against the roof of the mouth a device to temporarily alter the configuration of the palate to reduce the food-containing volume of the mouth and to reduce the quantity of food per bite.

6. A method according to claim 5, wherein said device includes a molded element for lowering the normally vaulted area of the roof of the mouth.

7. A method according to claim 6, wherein said molded element conforms to the contours of the roof of the mouth and has a thickened portion extending from the roof of the mouth toward the lower part of the mouth, to reduce the food-containing volume of the mouth.

8. A method according to claim 7, further including removably securing said device to the teeth adjacent to the roof of the mouth.

9. A method for reducing and controlling the weight of a person by reducing the person's food intake, comprising the steps of removably placing a molded element in fixed position against the roof of the person's mouth and temporarily altering the shape of the person's palate by lowering the vaulted area of the roof of the mouth to reduce the volume in the mouth available for food and the quantity of food per bite.

10. A method for reducing and controlling weight according to claim 9, wherein said molded element has a thickened central portion extending into the mouth cavity to reduce the volume in the mouth available for food, said central portion having a region of reduced thickness disposed adjacent to the front of the mouth and a region of increased thickness extending toward the back of the mouth.

11. A device for weight control, comprising:
    first means for positioning against the roof of a user's mouth to alter the configuration of the palate and to reduce the food-containing volume of the mouth;
    second means in operative relationship with said first means for removably supporting said first means in fixed position against the roof of the mouth; and
    wherein said first means defines a central, thickened portion extending from the roof of the user's mouth toward the lower part of the mouth to reduce the food-containing volume of the mouth, said central, thickened portion being thicker than remaining portions of said molded element.

12. A device as in claim 11 wherein said first means includes:
    a molded element defining an upper surface configured to fit the roof of the user's mouth, and a lower surface; and
    wherein said central, thickened portion is defined between said upper and lower surfaces to reduce the food-containing volume of the mouth.

13. A device as in claim 12 wherein said second means include second elements attached to said molded element for removably supporting said molded element in cooperation with the user's upper teeth.

14. A device as in claim 13 wherein said central, thickened portion includes a region of reduced thickness extending toward the front of the user's mouth and a region of increased thickness extending toward the back of the user's mouth when said molded element is removably positioned in fixed relationship against the roof of the user's mouth.

15. A method for weight control by reducing a person's food intake, comprising the steps of:

providing a device for reducing the food-containing volume of a person's mouth by lowering the normally vaulted area of the roof of the person's mouth;

positioning said device in fixed relationship against the roof of the person's mouth to reduce the food-containing volume of the person's mouth by lowering the normally vaulted area of the roof of the person's mouth; and removably securing said device to upper teeth of the person adjacent to the roof of the mouth.

* * * * *